United States Patent [19]

Sauerbier et al.

[11] Patent Number: 5,204,335
[45] Date of Patent: Apr. 20, 1993

[54] IFOSFAMIDE LYOPHILISATE AND PROCESS FOR ITS PREPARATION

[75] Inventors: Dieter Sauerbier, Werther; Uwe-Peter Dammann, Detmold; Otto Isaac, Hanau, all of Fed. Rep. of Germany

[73] Assignee: Asta Pharma Aktiengesellschaft, Fed. Rep. of Germany

[21] Appl. No.: 703,703

[22] Filed: May 21, 1991

Related U.S. Application Data

[63] Continuation of Ser. No. 418,089, Oct. 5, 1989, abandoned, which is a continuation of Ser. No. 113,154, Oct. 27, 1987, abandoned.

[30] Foreign Application Priority Data

Oct. 31, 1986 [DE] Fed. Rep. of Germany ....... 3637089

[51] Int. Cl.$^5$ .................. C07F 9/547; C07F 9/576; A61K 31/675
[52] U.S. Cl. ..................... 514/105; 514/79; 558/81; 544/1
[58] Field of Search .............. 558/81; 514/79, 105; 544/1

[56] References Cited

U.S. PATENT DOCUMENTS

| | | | |
|---|---|---|---|
| 3,732,340 | 5/1973 | Arnold et al. ................. | 568/12 |
| 4,537,883 | 8/1985 | Alexander et al. ............. | 514/110 |
| 4,623,742 | 11/1986 | Scheffler et al. ............. | 558/81 |

FOREIGN PATENT DOCUMENTS

| | | | |
|---|---|---|---|
| 1215649 | 12/1986 | Canada .......................... | 514/110 |
| 0083439 | 7/1983 | European Pat. Off. ......... | 568/12 |
| 2750207 | 11/1978 | Fed. Rep. of Germany ...... | 514/557 |
| 4203570 | 10/1987 | Fed. Rep. of Germany ...... | 514/110 |
| 1347582 | 2/1974 | United Kingdom ............. | 128/155 |

OTHER PUBLICATIONS

Remington Pharmaceutical Sciences Textbook, 15th Ed, 1975, Mack Publ. Co., Easton, Pa., pp. 1361, 1483, 1484.
Vanlerberghe et al., CA, vol. 92, 1980, 92:112612g.
Svito, CA, vol. 82, 1975, 85:47680e.
Norpoth et al., CA, vol. 83, 1975, 83:188122g.
"Lehrbuch der pharmazeutischen Technologie", Voigt, Rudolph, Chemie Verlag (Weinheim (1982), pp. 58–61, 431, 432 and 536.
"Lexikon der Hilfsstoffe fur Pharmazie, Kosmetik und Angrenzende Gebiete", Fiedler, Editio Cantor (Aulendorf 1981), pp. 588–589.
"Die Tablette", Ritschel, W. A., Editio Cantor (Aulendorf 1966), p. 88.

*Primary Examiner*—Alan L. Rotman
*Attorney, Agent, or Firm*—Cushman, Darby & Cushman

[57] ABSTRACT

Ifosfamide lyophilizate consisting substantially of ifosfamide and 0.1 to 17 parts by weight of a hexitol.

11 Claims, No Drawings

IFOSFAMIDE LYOPHILISATE AND PROCESS FOR ITS PREPARATION

This is a continuation of application Ser. No. 07/418,089, filed on Oct. 5, 1989, now abandoned, which was a continuation of application Ser. No. 07/113,154, filed Oct. 27, 1987, now abandoned.

The present invention relates to a novel form of ifosfamide which has improved properties.

BACKGROUND OF THE INVENTION

The chemical name of the active substance ifosfamide is 3-(2-chloroethyl)-2-(chloroethylamino)-tetrahydro-2H-1,3,2-oxazaphosphorin-2-oxide, which has the formula:

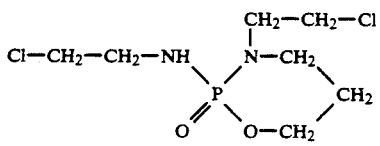

In common with cyclophosphamide, ifosfamide belongs to the chemical group of oxazaphosphorins and is used therapeutically for the treatment of tumor diseases.

Ifosfamide is a white crystalline powder which has a melting point of 48°-51° C. and which is highly hygroscopic. Ifosfamide begins to sinter at temperatures below its melting point and must, therefore, be stored at temperatures that are as low as possible (room temperature and below). In addition, contact with moisture in the air should be avoided whenever possible.

Ifosfamide dissolves in water to the extent of about 10 percent by weight, but is only stable to a limited extent in aqueous solution (maximum of 3 to 4 hours at 20° to 22° C. or 36 hours at 4° to 6° C.)

Ifosfamide is exclusively administered parenterally. It normally is supplied in injection vials which contain 200 to 5000 mg of ifosfamide in the form of a sterile crystallizate. This active ingredient is dissolved in water for injection purposes before administration, at a concentration of at most 4%. This solution is suitable for intravenous injection. For intravenous short infusion, the ifosfamide solution is dissolved in 500 ml of Ringer's solution or similar infusion liquid. The duration of the infusion is generally about 30 minutes, but may be 1 to 2 hours. In the case of the 24-hour infusion, the ifosfamide solution is, for example, dissolved in a total of 3 liters of 5% dextrose sodium chloride solution.

Ifosfamide gives rise to numerous practical problems during preparation and processing. During preparation of the sterile crystallized ifosfamide there is a change of physical characteristics. In particular, dosage accuracy during filling is greatly impaired by variable flow properties.

The processing of ifosfamide is further impeded by its hygroscopic properties and low melting point. When stored for a long period of time, the sterile crystallizate sinters and the rate of dissolution decreases. When the ifosfamide begins to sinter, this is accompanied by a decrease in clear solubility and in the pH of the solution, with simultaneous yellow coloration. Once this happens, therapeutic use is generally no longer possible.

SUMMARY OF THE INVENTION

The object of the present invention is therefore to make available a form of ifosfamide with improved properties, such as improved stability, shelf-life, dosability and solubility, which is easier to use, and which is in particular suitable for the preparation of injectable solutions.

It has now surprisingly been found that the previous disadvantages and difficulties associated with the use and storage of ifosfamide can be overcome by the use of a specific ifosfamide lyophilizate. In accordance with the present invention, therefore, a lyophilizate is produced by freeze drying an aqueous or aqueous/alcoholic (preferably aqueous/ethanolic) solution of ifosfamide and a hexitol. It has been found that the process of the invention alone, involving the use of a hexitol such as for example mannitol, produces an improved ifosfamide lyophilizate. By contrast, a mixture of ifosfamide and sodium chloride, such as is conventional for the dry filling of other oxazaphosphorins, does not yield a lyophilizate.

It is surprising that the ifosfamide lyophilizate of the invention has greater thermostability than the hitherto used ifosfamide dry crystallizate.

The difference between the conventional form of ifosfamide and the composition of the present invention is evident from the properties of the respective materials after storage. At 40° C., the conventional type of dry fillings of ifosfamide turn dark after only one month's storage. After 2 months the contents of the vial have sintered and turned yellow. At a storage temperature of 55° C., the dry filled ifosfamide fuses after as little as 4 days.

In contrast, the ifosfamide lyophilizate prepared according to the present invention displays neither discoloration nor any change in the consistency of the ifosfamide under the same storage conditions.

The dissolution rate of the ifosfamide lyophilizate produced by the present invention is also markedly increased in comparison to a conventional ifosfamide crystallizate. Whereas, the lyophilizate of the present invention dissolves immediately on addition of solvent, notwithstanding the length of time it has been stored, injection vials containing conventional dry filling have to be vigorously shaken for ½ to 3 minutes after introduction of the solvent. In those cases where dissolution is not immediately completed, as is the case with injection vials stored for a longer period of time, it even is necessary to let the solution stand for a few minutes. This impedes the use of the preparation in the hospital.

In contrast to sterile crystallizate, ifosfamide lyophilizate according to the present invention still shows optimum solubility properties after storage over several years.

In addition, the ifosfamide dry filling (i.e., the pure ifosfamide crystallizate) is far more sensitive to atmospheric moisture than is the lyophilizate. Thus, the ifosfamide dry filling liquefies at a relative humidity of less than 75%, whereas the lyophilizate of the present invention, although becoming moist, retains its outer form, even at 100% relative humidity.

Moreover, during filling of the sterile crystallizate, the risk of particulate or microbial contamination is far greater with the conventional material than with the lyophilizate.

In contrast, during preparation of the ifosfamide lyophilizate, sterile filtration of the solution only occurs immediately before filling into injection vials. This ensure greater microbiological safety than does the filling of sterile crystallizate. In addition, particulate impurities, which have occasionally given rise to complaints in the case of the dry filling, can be more reliably avoided by filtration of the solution.

Not only does the lyophilization of the ifosfamide improve the product, it is also less expensive than the cost of filling the sterile crystallizate.

For example, in accordance with the invention, an aqueous solution of ifosfamide containing 1 to 13 percent by weight of ifosfamide, as well as 0.1 to 17 parts by weight of a hexitol, for each part by weight of ifosfamide is freeze-dried. This aqueous solution advantageously contains 5 to 12 percent by weight, in particular 8 to 10 percent by weight of ifosfamide.

It is also possible to use corresponding ethanol-water solutions of ifosfamide in place of a purely aqueous solution (ethanol proportion of such a solution up to 45% weight by weight, for example 1–20% of ethanol). In such cases, the ethanol is, if possible, first removed under a vacuum before the remaining ice is sublimed. The conditions for the initial ethanol removal are for example: pressure $5 \times 10^{-1}$ mbar, temperature rising from $-25°$ to $-5°$ C. within 10 hours, subsequently being raised to $+22°$ C. The selection of freeze drying conditions depends on the thickness of the layer of material to be dried.

The amount of the hexitol in this aqueous or aqueous-ethanolic solution is generally 1 to 17, preferably 3 to 12, in particular 5 to 9 percent by weight. The amount of the hexitol may also be expressed in relation to the weight of ifosfamide, in which case the amount of the hexitol is 0.1 to 17, preferably 0.1 to 2.5, in particular 0.6 to 0.8 parts by weight of the hexitol for each part by weight of ifosfamide.

Hexitols which may be used include: mannitol, glucitol, sorbitol, such as D-sorbitol, dulcitol, allitol, altritol (for example D- and L-altritol), iditol (for example D- and L-iditol), their optically active forms (D- or L-forms) as well as the corresponding racemates. Use is preferably made of mannitol, such as D-mannitol, L-mannitol, DL-mannitol, sorbitol and/or dulcitol, and in particular preferably D-mannitol. The hexitol may also be mixtures of the hexitols mannitol, glucitol, sorbitol, dulcitol, allitol, altritol, iditol. Such a mixture could be, for example, mixtures of mannitol and sorbitol and/or dulcitol. Since dulcitol is less water-soluble than for example mannitol, the dulcitol content in the aqueous solution should for example not exceed 3 percent by weight. In contrast, mannitol and sorbitol may for example be mixed in all ratios.

In addition to a hexitol, it is also possible to add other conventional pharmaceutical auxiliary substances such as for example glycine, lactose, polyvinylpyrrolidone, glucose, fructose, albumin and equivalent body building substances. The total amount of such substances, i.e., hexitol and auxilliary substances, in the solution which is used for freeze-drying is for example 0–16.9 parts by weight, for example 0.1 to 7 parts by weight, for each part by weight of ifosfamide. Individually the amount of such auxiliary substances depends on the amount of the hexitol used in such a way that the total amount of the hexitol and of such other auxiliary substances in the finished lyophilizate is not more than 17 parts by weight, for each part by weight of ifosfamide. Should only 0.1 part by weight of the hexitol be present in the lyophilizate, it is therefore possible for up to 16.9 parts by weight of other auxiliary substances to be present; should for example 8.5 parts by weight of the hexitol be present, the amount of other auxiliary substances may for example be up to 8.5 parts by weight for each part by weight of ifosfamide.

To prepare the solution to be used for freeze-drying a vessel is charged with about 70 to 83% preferably 80% of the requisite amount of water or aqueous ethanol and the corresponding amount of ifosfamide and mannitol dissolved in succession (i.e., first the ifosfamide and then the mannitol) with continuous stirring or continuous agitation. After complete dissolution the solution is made up to the final volume, and the pH is measured. The pH of this solution should, for example, be between 4 and 7 after dilution. Advantageously a 4% ifosfamide solution is prepared.

The ifosfamide solution so obtained is then sterilized by filtration using pathogen-proof filters conventionally used for such purposes and then filled one or more vessels for freeze drying. Preferably, it is filled into appropriate containers for injection preparations. The storage time up to filling into the injection containers should not exceed a period of 3 to 4 hours, including the time taken to prepare the solution, if working is at room temperature (18° to 22° C.). Should freeze-drying not be possible immediately, such a solution, optionally also after filling into the injection containers, may for example be stored for up to 36 hours at lower temperatures, for example between $-5°$ and $+10°$ C., preferably $+4°$ to $+6°$ C., before freeze-drying begins.

To carry out the process of the invention, the so-obtained aqueous ifosfamide solution is filled into containers for injection preparations, for example ampoules or other glass vessels and the solution is freeze-dried.

For sterilization purposes, conventional pathogen-proof filters, for example conventional bacterial filters having a pore size of about 0.2 μm are used. When glass vessels or ampoules are used, these are first sterilized in the conventional manner.

The hexitols used (preferably mannitol, in particular D-mannitol) should conform to the requirements of the British Pharmacopoeia 1980. The hexitols should be as pyrogen-free as possible (pyrogens are fever-inducing endotoxins formed by bacteria).

The same applies to the ifosfamide used. The removal or destruction of the pyrogens is effected in conventional manner (for example the solution of active substance is treated with activated charcoal prior to sterile filtration). In addition, the injection water used should be sterile and pyrogen-free and conform to the requirements of the Deutsches Arzneibuch, 9th Edition 1986. The injection vessels may advantageously be those made from tubular glass or furnace glass of the IIIrd hydrolytic class (for example 10 R, 30 R and 50 H) (see in this connection Deutsches Arzneibuch, 9th Edition, 1986, pages 161–164 and DIN standard 58366 part 1 and 5).

Furthermore, the injection vessels as well as the additional auxiliary substances such as rubber stoppers and flanged caps conform to the requirements of DIN standard 58366, Part 2 and Part 3 as well as DIN 58367, Part 1.

The amounts of solution of the ifosfamide solutions to be used for lyophilization, in the appropriate containers (ampoules) or other containers for injection preparations, are, for example, between 1 and 500 ml, preferably 1 and 250 ml, and in particular 2 and 50 ml per container . The containers should in each case be s dimensioned that the lyophilizate contained therein may later be dissolved in a larger amount of liquid. They should therefore in general have a volume that is sufficiently large for the preparation of a ready-to-use final solution having about 2 to 5 times, preferably 2 to 4 times, and in particular 2 to 2.5 times the volume of the originally filled lyophilizate solution.

As already mentioned, it is preferred that the solution is freeze dried in ampoules used for injection purposes. Each ampoule or each glass vessel is advantageously filled with a single dosage unit of ifosfamide, so that the amount of ifosfamide in each glass vessel is for example between 100 mg and 10 g, preferably 200 mg to 5 g. Subsequently, the solution is freeze-dried in the customary manner in this glass vessel or ampoule. It is, however, also possible to lyophilize larger amounts of ifosfamide, i.e., a correspondingly larger solution volume of the ifosfamide solution in a correspondingly larger vessel and subsequently to subdivide or fill the lyophilizate obtained into correspondingly smaller dosages. The lyophilization itself is carried out in such a way that the ampoules or glass vessels or other vessels which contain the ifosfamide-hexitol solution are placed directly on a stand or on a rack in a freeze-drying chamber. Once the chamber has been closed, the ampoules or vessels are cooled to temperatures below $0°$ C., for example to temperatures between $-70°$ and $0°$ C., preferably $-50°$ to $-30°$ C., in particular $-45°$ to $-35°$ C. As soon as the solutions are completely frozen the freeze-drying chamber is progressively evacuated and drying commences. Firstly, the non-adsorptively bound solvent is removed at temperatures between $-30°$ and $+40°$ C., preferably $0°$ to $+30°$ C., in particular $+20°$ to $+30°$ C., for which purpose a pressure between $10^{-3}$ and 6, preferably $10^{-2}$ to 2, and in particular $10^{-1}$ to 1 mbar is selected. In all cases the temperature or temperature range refers to the temperature of the racks.

The process is so controlled that the heat applied via the plate temperature is completely used as heat of sublimation and the temperature of the froze ifosfamide-containing solution always remains below its eutectic temperature. The desired temperature of the plates in each case may for example be programmed via program disks or computers.

The time taken to remove this non-adsorptively bound solvent depends on the size of the individual containers and is, for example, between about 4 and 40 hours at a plate temperature of $+25°$ C. and a pressure of 0.8 mbar. Reference is made by way of example to the times given in the example below.

The complete removal of the non-adsorptively bound water is indicated as follows: Non-adsorptively bound water is present in the form of ice. Using a so-called pressure rise measurement, it is determined whether such water is still present in the lyophilizate. For this purpose, a valve is closed between the drying chamber and the condenser to which the vacuum pump is also connected. Any ice present would then quickly sublime and lead to a rise in pressure in the drying chamber.

In the case of pressure rise measurement, the pressure in the chamber after 15 minutes may rise to a maximum of 1 mbar from the starting value, for example 0.8 mbar. A rise in excess of this figure would indicate that the main drying has not yet been completed.

Residual adsorptively-bound solvent is then removed by post drying. This takes for example 3 to 12 hours at a vacuum of $10^{-1}$ to $10^{-4}$ mbar, in particular 3–4 hours at a vacuum of $10^{-3}$ to $10^{-4}$ mbar.

The lyophilization process is completed when the residual moisture (determined by the method of K. Fischer) is below 1%, preferably below 0.5%.

In particular, the post-drying for removal of adsorptively bound water takes place at temperatures between $0°$ and $40°$ C., preferably $10°$ to $35°$ C., in particular 20 to $30°$ C. and a pressure between $10^{-4}$ and $10^{-1}$, preferably $10^{-3}$ to $10^{-2}$, and in particular $10^{-3}$ to $5\times10^{-3}$ mbar, and this post-drying takes for example 2 to 36, preferably 6 to 24, and in particular 3 to 12 hours.

Following completion of the freeze-drying, the vessels containing the lyophilizate are sealed. All stages of the process of the invention are conducted under sterile conditions. The injection vials may be sealed for example after ventilation of the freeze-drying chamber to normal pressure through addition of dry, sterile air or nitrogen with special freeze-drying rubber stoppers which are treated with silicone to avoid abrasion and to improve lubricity.

DETAILED DESCRIPTION OF PREFERRED EMBODIMENT

The invention is illustrated by the following example:

EXAMPLE

The following solution is used for freeze-drying:

| | |
|---|---|
| Ifosfamide | 100 mg |
| D-mannitol | 70 mg |
| Water of injection ad | 1 ml |

The density of this solution is 1.0563 g/ml at $+6°$ C. and 1.0527 g/ml at $+20°$ C.

The amount of solution to be prepared depends on the appropriate filling and freeze-drying capacity.

Preparation of the solution:

A vessel is charged with 80% of water and appropriate amounts of ifosfamide and mannitol are added successively to the water with constant stirring. Following complete dissolution the mixture is made up to the final volume and the pH is measured.

The prepared solution is sterilized by filtration using pathogen proof filters conventionally used for this purpose (for example Sartorius SM 11107 or SM 11307, 0.2 μm pore size, Pall filter NRP (pore size 0.2 μm) and stored until filling while avoiding particulate and bacterial contamination. Storage at room temperature (20°–22° C.) should not exceed 3–4 hours, including the time required to prepare the solution. Should freeze-drying not take place immediately, the solution may be stored for about 36 hours at $+4°$ to $+6°$ C.

For purposes of sterile filtration, it is also possible to use conventional prefilters (for example Sartorius SM 13400 or Pall LPA) to protect the sterile filter.

Cleaning of the injection vials:

The injection vials are washed with hot and cold demineralized water and with air. All cleaning media are freed from suspended matter by filtration.

While avoiding re-contamination due to particles from the air, the vials are dried with hot air and sterilized (discontinuously at $180°$ C./2 hours).

The rubber stoppers used to close the injection vials are cleaned using demineralized water and for example a cleaning agent consisting of nonionic surfactants and phosphoric acid esters in aqueous solution.

The cleaned stoppers are rinsed using demineralized water or filtered demineralized water to free them of fibers and threads. The so-cleaned stoppers are then sterilized using steam.

The so-cleaned and sterilized injection vials are then filled aseptically with the ifosfamide solution and closed using the rubber stoppers.

Filling amounts:

|  | Filling amount | Volume used* |
|---|---|---|
| Ifosfamide 200 mg | 2 ml | 5 ml |
| 500 mg | 5 ml | 12.5 ml |
| 1 g | 10 ml | 25 ml |
| 2 g | 20 ml | 50 ml |
| 5 g | 50 ml | 125 ml |

*For the subsequent dilution of the lyophilizate

The filling volumes should not exceed the following limits:

| Filling volume | Limiting value of individual filling volumes | Average limiting value of the filling volume |
|---|---|---|
| 2 ml | 1.9–2.1 ml | 1.95–2.05 ml |
| 5 ml | 4.8–5.2 ml | 4.9–5.1 ml |
| 10 ml | 9.7–10.3 ml | 9.85–10.15 ml |
| 20 ml | 19.4–20.6 ml | 19.7–20.3 ml |
| 50 ml | 48.5–51.5 ml | 49.25–50.75 ml |

The filling volumes must be statistically monitored, with the filling volume per filling station being measured at least once every 30 minutes.

The filled injection vials are frozen as quickly as possible to −40° C.

The conditions for freeze-drying differ according to the size of the injection vials. The following are representative examples:

Duration of main drying at a plate temperature of +25° C. and 0.6 mbar:

| ca. 6–8 hours for vessels with 200 mg ifosfamide |
| ca. 10–12 hours for vessels with 500 mg ifosfamide |
| ca. 10–14 hours for vessels with 1000 mg ifosfamide |
| ca. 20–28 hours for vessels with 2000 mg ifosfamide |
| ca. 34 hours for vessels with 5000 mg ifosfamide |

Duration of post drying ca. 3–4 hours under vacuum of $5 \times 10^{-4}$ mbar, at a plate temperature of +25° C.

The residual moisture (determined by the method of K. Fischer) should be less than 0.5%.

Following completion of freeze-drying the injection vials are sealed.

To fix the rubber stoppers flanged caps are superimposed and rolled on. The finished injection vials are checked for mechanical defects (cracks, faulty closure, etc.).

What is claimed is:

1. A lyophilized preparation comprising ifosfamide and 0.1 to 17 parts by weight of a hexitol selected from the group consisting of mannitol, dulcitol and sorbitol for each part by weight of ifosfamide.

2. A lyophilized preparation as set forth in claim 1 including other conventional pharmaceutical auxiliary substances, the total amount of hexitol and said other conventional pharmaceutical auxiliary substances being 0.1 to 17 parts by weight for each part by weight of ifosfamide.

3. A lyophilized preparation according to claim 1 in which the hexitol is mannitol.

4. A process for the preparation of an ifosfamide lyophilizate which comprises freezing an aqueous or aqueous-ethanolic solution of ifosfamide containing 1 to 13 percent by weight of ifosfamide and 0.1 to 17 parts by weight of a hexitol selected from the group consisting of mannitol, dulcitol and sorbitol for each part by weight of ifosfamide as well as 0 to 16.9 parts by weight for each part by weight of ifosfamide, of other conventional pharmaceutical auxiliary substances, the total amount of said hexitol and said other conventional pharmaceutical auxiliary substances, the total amount of said hexitol and said other conventional pharmaceutical auxiliary substances being up to 17 parts by weight for each part by weight of ifosfamide, at between −70° and 0° C. and removing the water from the so-obtained product while it is in the frozen state.

5. A process according to claim 4 in which initially non-adsorptively bound water is first removed from the frozen solution at a temperature between −30° and +40° C. and a pressure between $10^{-3}$ and 10 mbar and subsequently adsorptively bound water is removed at a temperature between 0° and 40° C. and a pressure between $10^{-4}$ to $10^{-1}$ mbar.

6. A process as set forth in claim 5 in which non-adsorptively bound water is first removed from the frozen solution at a temperature between +20° and +30° C. and a pressure between $10^{-1}$ and 1 mbar and adsorptively bound water is removed at a pressure between $10^{-3}$ and $10^{-4}$ mbar.

7. A process as set forth in claim 5 in which the solution is an aqueous/ethanolic solution and ethanol is removed before removal of water.

8. A process as set forth in claim 7 in which the solution contains up to 45% ethanol.

9. A process as set forth in claim 7 or claim 8 in which the ethanol is removed at a pressure of $5 \times 10^{-1}$ mbar and a temperature between 25° and +5° C.

10. A process according to claim 5 in which the hexitol is mannitol.

11. Ifosfamide lyophilizate produced by a process comprising freezing an aqueous or aqueous-ethanolic solution of ifosfamide containing 0.1 to 17 parts by weight of a hexitol selected from the group consisting of mannitol, dulcitol and sorbitol for each part by weight of ifosfamide as well as 0 to 16.9 parts by weight for each part by weight of ifosfamide, of other conventional pharmaceutical auxiliary substances, the total amount of said hexitol and said other conventional pharmaceutical auxiliary substances being up to 17 parts by weight for each part by weight of ifosfamide, at between −70° and 0° C. and removing the water from the so-obtained product while it is in the frozen state.

* * * * *